(12) United States Patent
Durfee et al.

(10) Patent No.: US 11,241,171 B2
(45) Date of Patent: Feb. 8, 2022

(54) DEVICES, SYSTEMS AND METHODS FOR MONITORING NEUROMUSCULAR BLOCKAGE

(71) Applicant: REGENTS OF THE UNIVERSITY OF MINNESOTA, Minneapolis, MN (US)

(72) Inventors: William Keith Durfee, Edina, MN (US); Paul Anthony Iaizzo, White Bear Lake, MN (US); Jesus Arturo Cabrera, Minneapolis, MN (US); Jenna Christine Iaizzo, Minneapolis, MN (US); John Mehawej, Robbinsdale, MN (US); Kevin Ruda, St. Paul, MN (US); Jason Paul McConnell, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 28 days.

(21) Appl. No.: 15/325,959

(22) PCT Filed: Jul. 16, 2015

(86) PCT No.: PCT/US2015/040733
§ 371 (c)(1),
(2) Date: Jan. 12, 2017

(87) PCT Pub. No.: WO2016/011244
PCT Pub. Date: Jan. 21, 2016

(65) Prior Publication Data
US 2017/0164875 A1  Jun. 15, 2017

Related U.S. Application Data

(60) Provisional application No. 62/025,236, filed on Jul. 16, 2014.

(51) Int. Cl.
*A61B 5/11* (2006.01)

(52) U.S. Cl.
CPC ................................ *A61B 5/1106* (2013.01)

(58) Field of Classification Search
CPC ................ A61B 5/0488; A61B 5/1106; A61B 2018/00839; A61B 2018/00434;
(Continued)

(56) References Cited

U.S. PATENT DOCUMENTS 5,131,401 A    7/1992  Westenskow et al.
5,957,860 A *  9/1999  Rodiera Olive ..... A61B 5/1106
                                                600/546
(Continued)

FOREIGN PATENT DOCUMENTS

WO    WO 2005/051201 A1    6/2005
WO    WO 2011/159883 A1    12/2011

OTHER PUBLICATIONS

International Search Report for corresponding International Application No. PCT/US2015/040733 dated Oct. 16, 2015; 4 pages.
(Continued)

*Primary Examiner* — Patrick Fernandes
(74) *Attorney, Agent, or Firm* — Patterson Thuente Pedersen, P.A.

(57) ABSTRACT

Embodiments relate to devices, systems and methods for monitoring neuromuscular blockage. In an embodiment, a neuromuscular blockage monitoring system comprises a patch device comprising a unitary patch body, at least two electrodes and at least one sensor, the at least one sensor arranged between the at least two electrodes on the unitary patch body; and a stimulator device operatively coupled to the patch device and configured to provide at least one electrical signal to the at least two electrodes to stimulate a muscle motor point and to receive a signal from the at least
(Continued)

one sensor related to a result of the stimulation of the muscle motor point.

20 Claims, 12 Drawing Sheets

(58) Field of Classification Search
CPC .............. A61N 1/0051; A61N 1/36071; A61N 1/36139; A61N 1/36017
See application file for complete search history.

(56) References Cited

U.S. PATENT DOCUMENTS

| | | | | |
|---|---|---|---|---|
| 6,088,618 | A * | 7/2000 | Kerver | A61N 1/37211 |
| | | | | 607/30 |
| 2008/0281379 | A1 * | 11/2008 | Wesselink | A61N 1/36135 |
| | | | | 607/60 |
| 2010/0004715 | A1 * | 1/2010 | Fahey | A61H 39/002 |
| | | | | 607/48 |
| 2011/0230782 | A1 * | 9/2011 | Bartol | A61B 5/0488 |
| | | | | 600/546 |
| 2012/0245482 | A1 | 9/2012 | Bolser et al. | |
| 2014/0107524 | A1 * | 4/2014 | Brull | A61B 5/0488 |
| | | | | 600/554 |

OTHER PUBLICATIONS

Written Opinion of the International Searching Authority for corresponding International Application No. PCT/US2015/040733 dated Oct. 16, 2015; 5 pages.
International Preliminary Report on Patentability, Application No. PCT/US2015/040733, dated Jan. 26, 2017, 7 pages.
European Communication, Application No. 15747874.4, dated Jan. 31, 2018, 5 pages.
European Communication, Application No. 15747874.4, dated Sep. 11, 2018, 3 pages.

* cited by examiner

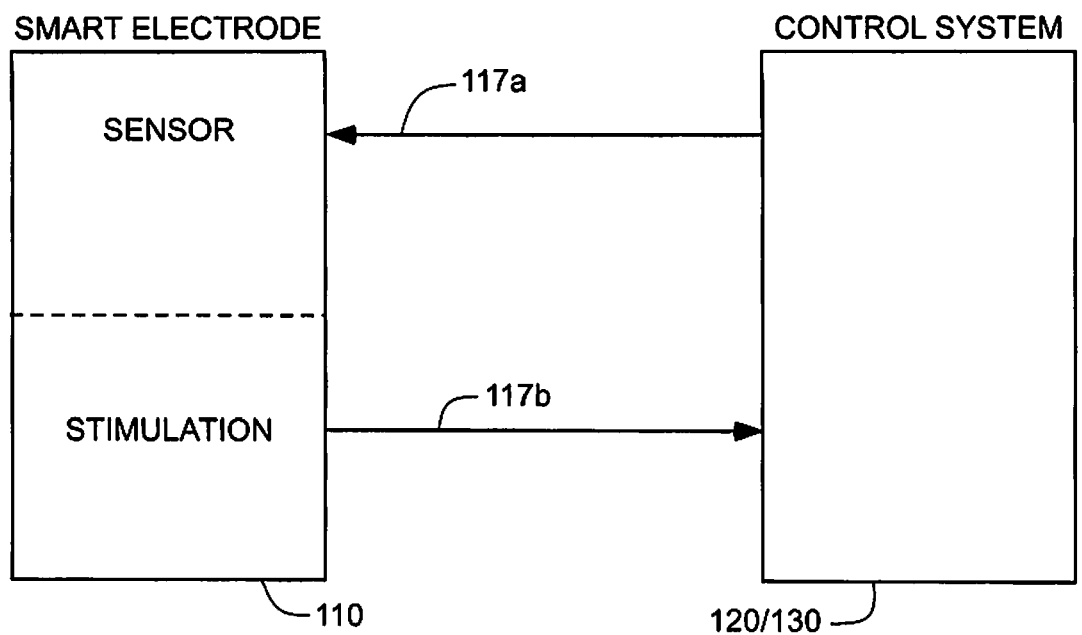

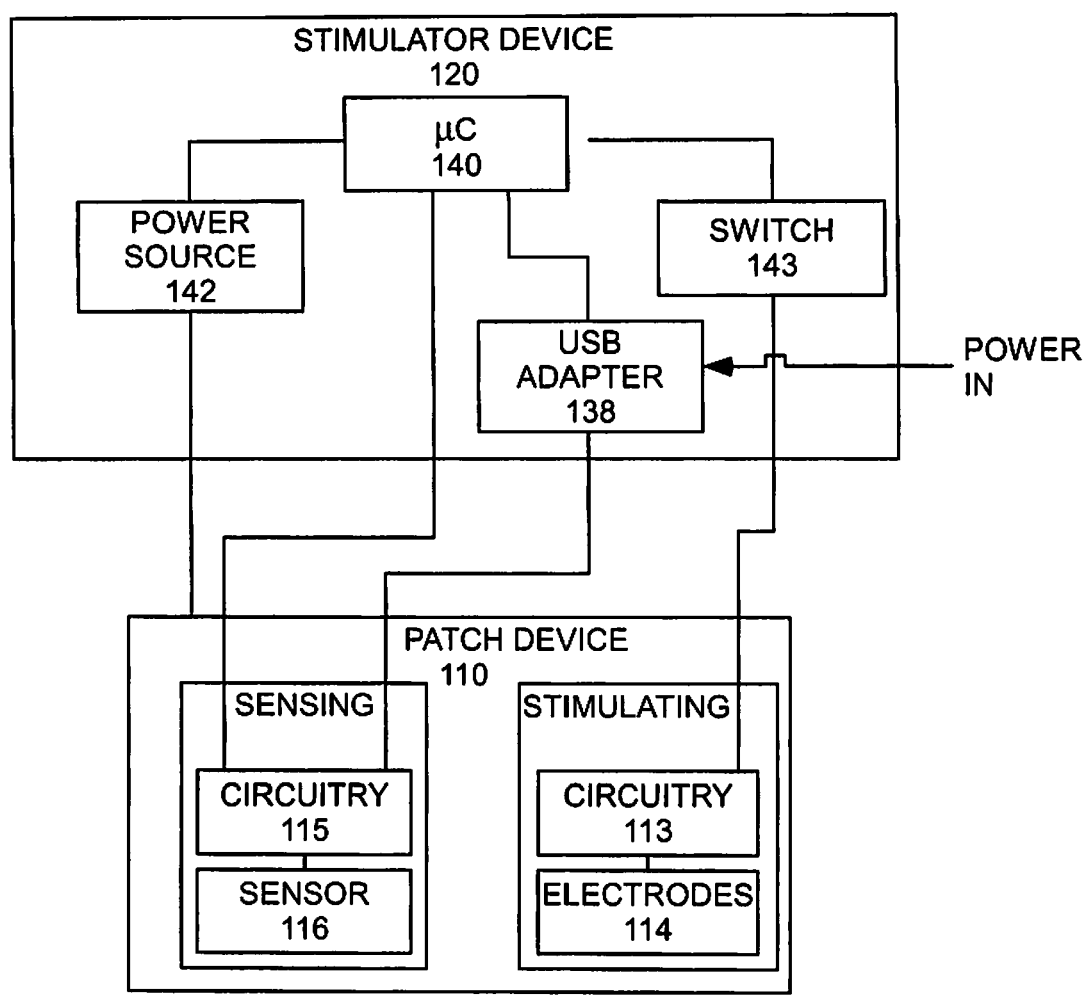

DEVICES, SYSTEMS AND METHODS FOR MONITORING NEUROMUSCULAR BLOCKAGE

CROSS-REFERENCE TO RELATED APPLICATIONS

This application is a National Stage Application of PCT/US2015/040733, filed on 16 Jul. 2015, which claims benefit of U.S. Provisional Application No. 62/025,236, filed on 16 Jul. 2014, and which applications are incorporated herein by reference in their entireties. A claim of priority to all, to the extent appropriate, is made.

TECHNICAL FIELD

Embodiments relate generally to medical devices, and more particularly to medical devices comprising sensors for monitoring patient neuromuscular blockage status, e.g., during surgery or other procedures.

BACKGROUND

During general anesthesia, a patient is given two types of drugs, anesthetics and neuromuscular blocking agents (NMBAs), the latter also known as neuromuscular blocking drugs (NMBD). The anesthetics cause unconsciousness so there is no recollection of the surgery, while NMBAs paralyze skeletal muscles to suppress any involuntary movements the body might have. At the start of a surgery, quick-acting NMBAs are given, and there is a critical time when the patient will need to be intubated to allow for mechanical breathing. Once the patient is intubated, the surgeon starts the surgical procedure and more NMBAs are given as needed during the procedure. There is a fine line as to the amount of paralysis a patient can take: too much and there can be permanent nerve damage, too little and the surgeon cannot do his or her job properly. Once the surgery is close to finishing, an anesthesiologist will put reversal drugs into the body that counteract the NMBAs. There is a constant need to know how much block is in a patient at a given time, but first it is important to know what NMBAs actually do in the body.

A muscle movement occurs when an action potential from the brain travels through the nerve to the synapse where it meets the innervated muscle. Once the synapse gets the action potential, it releases a chemical called acetylcholine (ACh). The muscle has chemical receptors that will cause a muscle contraction once ACh binds to the receptor. NMBAs will also bind to the chemical receptors on the muscle. This will block the muscle from contracting even though ACh was released by the nerve. The level of block in a patient is determined by the percentage of receptors that the NMBA binds to.

A current method of determining the level of paralysis in a patient is to do the Train of Four (TOF) test using a peripheral nerve stimulator (PNS). TOF is four electrical pulses through the ulnar nerve, facial nerve, or the tibial nerve. Four muscle twitches are observed on the corresponding muscles, and if NMBAs are present a fade (i.e., a decreasing muscle response) can be observed. This fade is how the level of paralysis in a patient is often characterized. Looking at the number of twitches that are observable, and the ratio in strength of the fourth twitch over the first twitch (called the TOF ratio) will give a good indication of how much block is in the body.

Literature has shown it is safe to move a patient from the operating room to a recovery room when the TOF ratio is above 90%. A TOF ratio below 90% will increase the likelihood of a patient experiencing post operative residual paralysis (PORP). Symptoms of PORP include difficulty breathing and swallowing, and muscle weakness; in the worst-case scenario, re-intubation can be necessary.

There are approximately 17 million surgeries each year in which patients are given neuromuscular blocking agents to induce paralysis. The majority of these surgeries use a PNS to conduct the TOF on a patient. The biggest drawback of this measurement, however, is that the TOF ratio is evaluated qualitatively by the anesthesiologist, either visually or tactilely. That means the anesthesiologist will manually look or feel the muscle twitching to determine if the patient is ready to be extubated and leave the operating room. Other clinical cues are often used, such as if the patient can lift his or her head for a few seconds, but one can never truly know how much NMBAs are in a patient because the evaluation does not take into account the NMBAs that are in the vascular system waiting to bind to the muscle receptors.

Many current literature articles discuss that for an experienced anesthesiologist it is very difficult, if not impossible, to objectively determine a difference in the TOF ratio above 40%. That is an unacceptably large margin of error. While anesthesiologists have extensive training, it was estimated that patients had a TOF ratio of below 70% in 30% of surgeries. This can range from minor to major symptoms, but still supports the fact that a new solution to measure NMBAs is severely needed.

Other products have focused on meeting the need for a quantitative block monitoring system, though with marginal success. While these systems can be very accurate, they also can be cumbersome and difficult to use. For example, one system referred to as the TOF-watch requires two electrodes to be attached separately to the patient, in addition to an accelerometer on the thumb. Adding even more complexity and time consumption, the patient's fingers also need to be taped down, along with many of the wires, in order to secure the system. Furthermore, a rigid bar that holds the thumb in place is recommended when calibrating the TOF-watch. When comparing the TOF-watch with the previous system of just a PNS and quick application of two electrodes and connections, the TOF-watch setup is very cumbersome.

These encumbrances are critical because anesthesiologists are severely pressed for time when starting a surgery. If everything goes well the TOF-watch setup may only slightly delay the surgery, but every additional step is one more area that can potentially cause a longer delay, particularly if a surgeon is under time pressure and eager to begin the procedure.

Another drawback of the PNS and other conventional systems is that test application and results must be documented manually. Given that the tests may be administered frequently (e.g., every fifteen minutes for some drugs, and often more frequently toward the anticipated end of a procedure), the documentation can be time-consuming and take the anesthesiologist away from other important tasks.

SUMMARY

Embodiments relate to devices, systems and methods for monitoring neuromuscular blockage. In an embodiment, a neuromuscular blockage monitoring system comprises a patch device comprising a unitary patch body, at least two electrodes and at least one sensor, the at least one sensor arranged between the at least two electrodes on the unitary patch body; and a stimulator device operatively coupled to the patch device and configured to provide at least one electrical signal to the at least two electrodes to stimulate a muscle motor point and to receive a signal from the at least one sensor related to a result of the stimulation of the muscle motor point.

In an embodiment, a kit comprises at least one patch device comprising a unitary patch body, at least two electrodes and at least one sensor, the at least one sensor arranged between the at least two electrodes on the unitary patch body; a stimulator device operatively coupled to the patch device and configured to provide at least one electrical signal to the at least two electrodes to stimulate a muscle motor point and to receive a signal from the at least one sensor related to a result of the stimulation of the muscle motor point; and user instructions related to the at least one patch device and the stimulator device.

The above summary is not intended to describe each illustrated embodiment or every implementation of the present invention. The figures and the detailed description that follow more particularly exemplify these embodiments.

BRIEF DESCRIPTION OF THE DRAWINGS

Embodiments may be more completely understood in consideration of the following detailed description in connection with the accompanying drawings, in which:

FIG. 1A is a block diagram of a neuromuscular blockage monitoring system according to an embodiment.

FIG. 1B is a block diagram of a neuromuscular blockage monitoring system according to an embodiment.

FIG. 3D is a functional block diagram of a stimulator device and a patch device according to an embodiment.

Figure 2A:
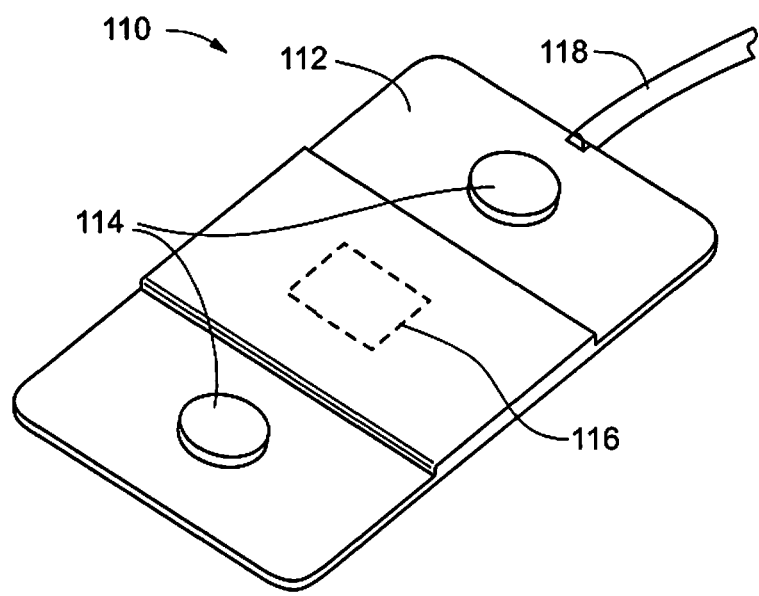
FIG. 2A is a diagram of a patch device according to an embodiment.

While embodiments are amenable to various modifications and alternative forms, specifics thereof have been shown by way of example in the drawings and will be described in detail. It should be understood, however, that the intention is not to limit to be limited to or by the particular embodiments depicted and described. On the contrary, the intention is to cover all modifications, equivalents, and alternatives falling within the spirit and scope of the appended claims.

DETAILED DESCRIPTION

Embodiments relate to devices, systems and methods for noninvasive, automated determination of the level of neuromuscular blockade in a patient. In embodiments, a single patch device comprises electrodes and at least one sensor. The patch device can comprise an adhesive or other material for temporarily and selectively coupling the patch device to a peripheral nerve area of a patient, such as proximate the ulnar nerve, facial nerve or tibial nerve. The patch device can be operatively and communicatively coupled to a computing device, such as a computer, laptop, tablet, smartphone, FDA, or other device, which can be used to control the patch device in use.

In operation, such as during a surgery or other procedure or setting, an anesthesiologist or other medical professional can, via the computing device, initiate a stimulation routine by the electrodes of the patch device and view a resulting signal from the sensor sensing a response to the stimulation routine. Viewing the resulting signal can include viewing the actual data related to the stimulation, such as a graphical depiction of the muscular response detected by the sensor, as well as viewing an analysis of the test results provided by the computing device (e.g., a calculation of the TGF ratio and/or other metrics). The computing device can record the details of the test and the related results, which can comprise providing information related to the test and results to an electronic medical records (EMR) system.

Referring to FIGS. 1A and 1B, a block diagram of an embodiment of a neuromuscular blockage monitoring system 100 is depicted. System 100 can comprise a patch device 110 (also referred to herein as a "smart electrode"; see FIG. 1B), a stimulator device 120 and a computing device 130. Computing device 130, or stimulator device 120 and computing device 130 collectively, are also referred to herein as a "control system"; see FIG. 1B. Patch device 110 can be operatively coupled with stimulator device 120, which in turn can be operatively coupled with computing device 130. These couplings can be wired, wireless or a combination of wired and wireless.

For example, in one embodiment the connection between patch device 110 and stimulator device 120 is wired, such that power to patch device 110 can be provided by stimulator device 120. In one particular example depicted in FIG. 1B, two wires 117a and 117b couple patch device 110 to stimulator device 120, with one or more wires sharing functionality (e.g., sensing and stimulation wires can be combined). 1n other embodiments, more (e.g., three, four or more) or fewer wires can couple patch device 110 to stimulator device 120. The connection between stimulator device 120 and computing device 130 also can be wired. In other embodiments, one, some or all of the connections can be wireless, such as via WIFI, BLUETOOTH, near-field communication, radio frequency (RE) or some other suitable wireless connection. In embodiments utilizing wireless communications, one, some or all of patch device 110, stimulator device 120 and computing device 130 can be independently powered, either via one or more batteries, an AC connection (e.g., 120 V, 220 V), or some other suitable power source.

While stimulator device 120 and computing device 130 are depicted as two separate devices in FIG. 1A, in other embodiments they can be integrated in a single unit (FIG. 1B) and/or integrated with some other medical device or computing device. For example, computing device 130 can comprise a general computer or a computing device that carries out other tasks, such as monitoring of patient vital signs, administration of drugs or fluids, or some other process. In still other embodiments, stimulator device 120, one or more patch devices 110, and optionally one or more cables for operative coupling therewith can be provided as a system or kit, with stimulator device 120 coupleable with virtually any computer, tablet, smartphone or other computing device 130 owned or obtained separately by a user or medical facility. Such a system or kit can further comprise hardcopy or digital operating instructions. Patch device 110, stimulator device 120 and computing device 130 are discussed in more detail below.

Figure 2B:
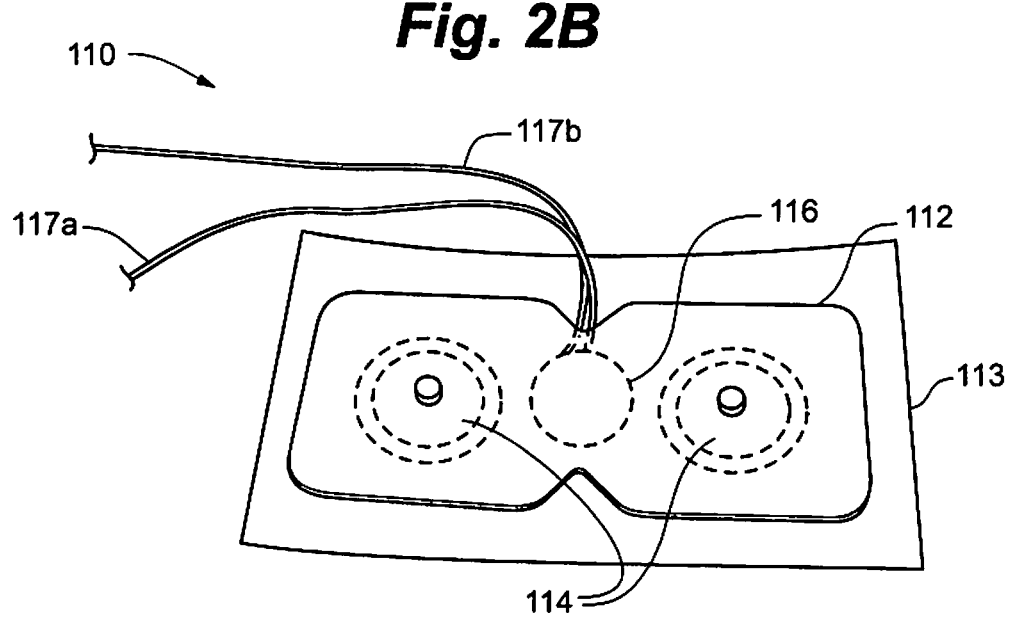
FIG. 2B is a depiction of a prototype patch device according to an embodiment.

Referring also to FIGS. 2A and 2B, patch device 110 can comprise a patch body 112, at least one electrode 114 and at least one sensor 116. Patch device 110 comprises all of the elements needed to quantify the amount of neuromuscular block in a patient and therefore is very versatile, able to be placed on many motor points of muscles. Instead of stimulating a large nerve bundle and measuring the reaction at another location as in conventional devices, patch device 110 can comprise a smart electrode to stimulate the nerves that are proximal to the innervated muscle and measure the muscle reaction at the same place. Co-locating the electrodes 114 and sensor 116 in this way provides many advantages, including a simple, easy to use system that is efficient to apply. The automation features discussed later herein provide additional advantages.

The embodiments of FIGS. 2A and 2B comprise a wired connection between patch device 110 and stimulator device 120, via cable 118 in FIG. 2A and wires 117*a* and 117*b* in FIG. 2B, though cable 118 or wires 117*a* and 117*b* can be omitted in other embodiments. Cable 118, or wires 117*a* and 117*b*, can provide power to patch device 110 and also communicate signals between patch device 110 and at least one of stimulator device 120 and computing device 130. Cable 118 can comprise a single cable as in FIG. 2A, or multiple cables or wires 117*a* and 117*b* as in FIG. 2B and in other embodiments.

Patch body 112 can be flexible or semi-flexible in embodiments, such that patch body 112 can easily conform to the shape of an area of a patient's body to which patch device 110 is applied. While patch body 112 is depicted as being generally rectangular, a variety of other shapes can be implemented in other embodiments, including square, round, oval, oblong, and butterfly, among others. Patch body 112 can be made available in various shapes to more easily conform to particular areas of the body (e.g., a circular patch body may be suited for the facial nerve area, while a rectangular patch body may be suited for the ulner nerve area) as well as in various sizes to be easily used for any of neonatal, pediatric and adult applications.

Additionally, while patch body 112 is depicted in FIGS. 2A and 2B as a single unitary piece, patch body 112 can comprise a plurality of portions in other embodiments. For example, in one embodiment patch body 112 comprises three portions, one for each of two electrodes 114 and sensor 116, with the three portions coupled together by cable 118. The plurality of portions can be provided as a unitary body that is selectively separable (e.g., by tearing along perforations provided between the portions) or partially separable (e.g., coupled by one or more elastic portions) for flexibility in positioning in application to a patient. Such configurations may enable more precise placement of the various components relative to a patient's particular anatomy, or provide other advantages.

In still other embodiments, a single configuration of patch device 110 can be provided, suitable for use with any of the ulnar, facial or tibial nerves, an advantage of such an embodiment being provision of a single device suitable for multiple anatomical applications.

In embodiments, patch body 112 can comprise a plurality of layers. As depicted in FIG. 2B, patch body 112 can comprise an adhesive layer or area to temporarily and selectively couple patch device 110 to the surface of a patient's skin on the reverse or under-side of patch body 112. Removing a protective backing layer 113 can expose the adhesive for application to the surface of a patient's skin. In other embodiments, backing layer 113 can be incorporated into an overall packaging for patch device 110, such that opening and removing the packaging around patch device 110 also exposes the adhesive layer. Instead of or in addition to an adhesive layer, other devices and methodologies can be used to secure patch body 110 to a patient, such as adhesive tape applied over patch body 112 and/or cable 118 or wires 117*a* and 117*b*, an elastic band or cuff, a VELCRO strip or band, adhesive tabs coupled with patch body 112, a wearable device (e.g., a bracelet, band, glove, sleeve, hat, etc.), or some other suitable securing device or mechanism.

In general, the adhesive or other securing device is easily applied, sufficiently secure to provide good contact between electrodes 114 and the patient's skin, nonirritating, and sufficiently easy to remove after use. Medical grade adhesives are suitable in example embodiments. Interior or intermediate layers of patch body 112 can comprise a substrate, traces, wires and other components configured to operatively and electrically couple cable 118 with electrodes 114, sensor 116 and other elements and circuits of patch device 110. A top layer can cover patch body 112 and, in embodiments, form a housing or enclosure along with a bottom layer. In some embodiments, a top or other layer of patch body 112 can comprise an antenna, such as in embodiments in which wireless communications are used, or other circuitry or components.

Electrodes 114 are at least partially exposed from patch body 112 for coupling with a patient's skin in a manner sufficient to enable electrical pulses to be delivered in use. In embodiments, electrodes 114 can comprise silver (Ag) electrodes, silver chloride (AgCl) electrodes, or some other suitable material composition. In the embodiment of FIGS. 2A and 2B, patch device 110 comprises two electrodes 114 on opposite ends or sides of patch body 112, but other configurations can be used in other embodiments. For example, patch device 110 can comprise more or fewer electrodes in other embodiments, and at least one of the electrodes 114 can be differently shaped, arranged more or less proximate a perimeter of patch body 110, or spaced apart from the other electrode(s) or sensor 116 by a greater or lesser distance. In still other embodiments, the relative arrangement of electrodes 114 and cable 118 can be altered, such that cable 118 is coupled to patch body 112 on an adjacent side to the one depicted in FIG. 2A, intermediate electrodes 112 and more proximate sensor 116 as in the embodiment of FIG. 2B. Such a configuration could reduce a length of cable 118 or other wiring or circuitry used to provide contact with each of electrodes 114 and sensor 116.

Sensor 116 comprises at least one sensing element in embodiments, such as a piezoelectric sensing element, accelerometer, stretch sensor or other sensing element suitable for sensing a muscle response to electrical stimulation. In one embodiment, a piezoelectric sensor can be used, at least in part because of its favorable signal to noise ratio (SNR), small package, inexpensiveness, and the fact that it is a passive sensor. In operation, a piezoelectric sensor can transduce a mechanical muscle reaction to electrical nerve stimulation provided by electrodes 114 and provide an output signal related to an occurrence or degree of muscle reaction. The output signal typically will be an analog output signal, which can be converted to a digital signal by analog-to-digital converter (ADC) in stimulator device 120 or elsewhere in system 100.

Sensor 116 is depicted as being embedded or sandwiched within patch body 112 in the embodiments of FIGS. 2A and 2B, while in other embodiments, sensor 116 can be otherwise arranged on or within patch body 112 and/or can comprise external contacts for coupling with a patient's skin. In FIGS. 2A and 2B, sensor 116 is arranged between electrodes 114, but other relative arrangements of sensor 116 and one or more electrodes 114 can be implemented in other embodiments, such as to accommodate a patch body 112 design or arrangement, or to be customized for a particular anatomical area.

Figure 3A:
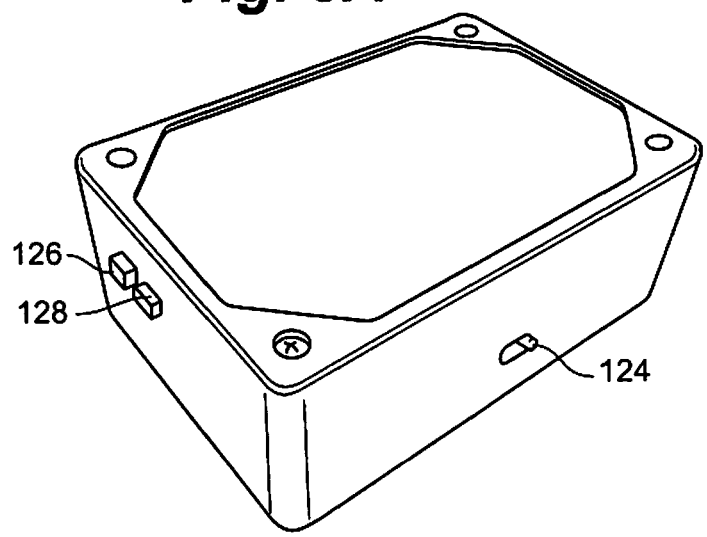
FIG. 3A is a diagram of an exterior of a stimulator device according to an embodiment.
Figure 3B:
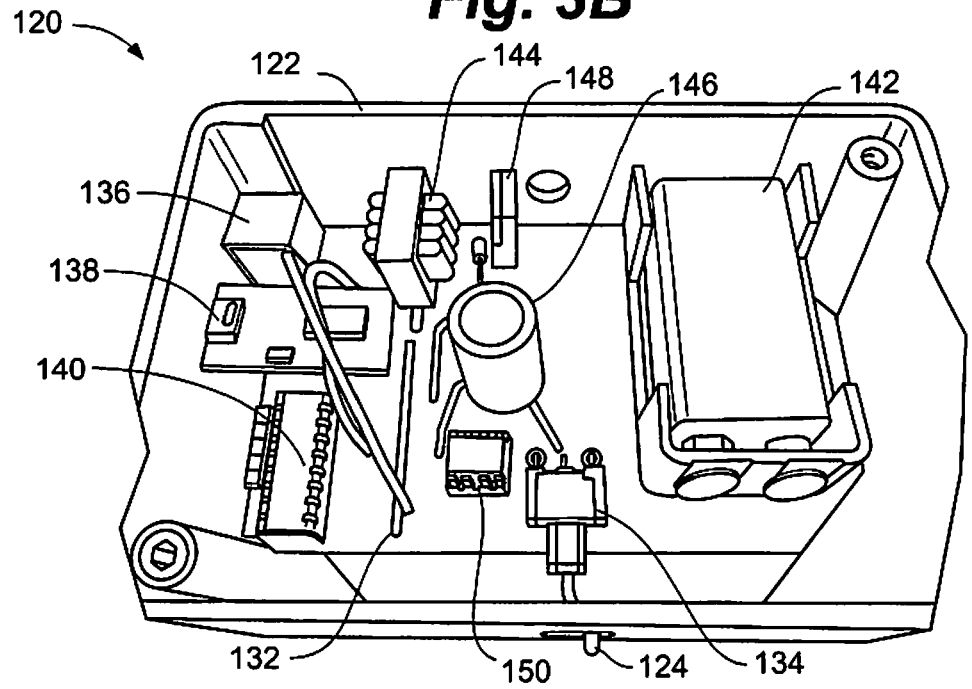
FIG. 3B is a diagram of interior components of the stimulator device of FIG. 3A according to an embodiment.

Referring again to FIGS. 1A and 1B and also to FIGS. 3A and 3B, a prototype of stimulator device 120 is depicted in FIGS. 3A and 3B. Stimulator device 120 can be coupled with patch device 110 via cable 118 or wires 117a and 117b, wirelessly, or via some other device or methodology. Stimulator device 120 comprises a housing 122, an on/off switch 124, a port 126 for operative coupling with patch device 110, and a port 128 for operatively coupling with computing device 130. Ports 126 and 128 can comprise a variety of different types of ports for coupling with a variety of different cables and technologies. In one embodiment, port 1126 comprises a mini-DIN port, and port 128 comprises a USB port. Ports 126 and 128, or other or additional ports of stimulator device 120, can also comprise different ports for interfacing with different cables or technologies in other embodiments, such as mini-jacks, firewire, coaxial, HDMI, mini-B, pinned, or virtually any other kind of port or cable. One or both of ports 126 and 128 can be omitted in embodiments in which wireless or a combination of wired and wireless communications are used.

In FIG. 3B, an interior of a prototype of stimulator device 120 is depicted according to an embodiment. Stimulator device 120 comprises a printed circuit board (PCB) 132, on which are mounted a switch mechanism 134 of switch 124, a mini-DIN adapter 136 coupled with port 126, and a USB adapter 138 coupled with port 128. A microcontroller 140, power source 142, transformer 144, voltage regulator 146, MOSFET (metal-oxide-semiconductor field-effect transistor) 148, and operational amplifier 150 are also mounted on PCB 132. The particular arrangement and elements of FIG. 3B (and FIG. 3C) are but an example embodiment of stimulator device 120, and the operation and features of stimulator device 120 can be implemented in many other ways, with more or fewer circuits and components, in other embodiments without departing from the spirit or scope of the claims.

Switch 124 and switch mechanism 134 control the power on or off status of stimulator device 120. Adapters 136 and 138 couple ports 126 and 128, respectively, with microcontroller 140 and other elements of stimulator device 120 and/or system 100. Power source 142 can comprise one or more batteries, such as a 9V battery in the embodiment of FIG. 3B, coupled with voltage regulator 146, which can be a 5V regulator in one embodiment. In still other embodiments, power source 142 can instead or in addition comprise an external connection to a 120 V, 220 V or other power source.

Figures 1, 3C:
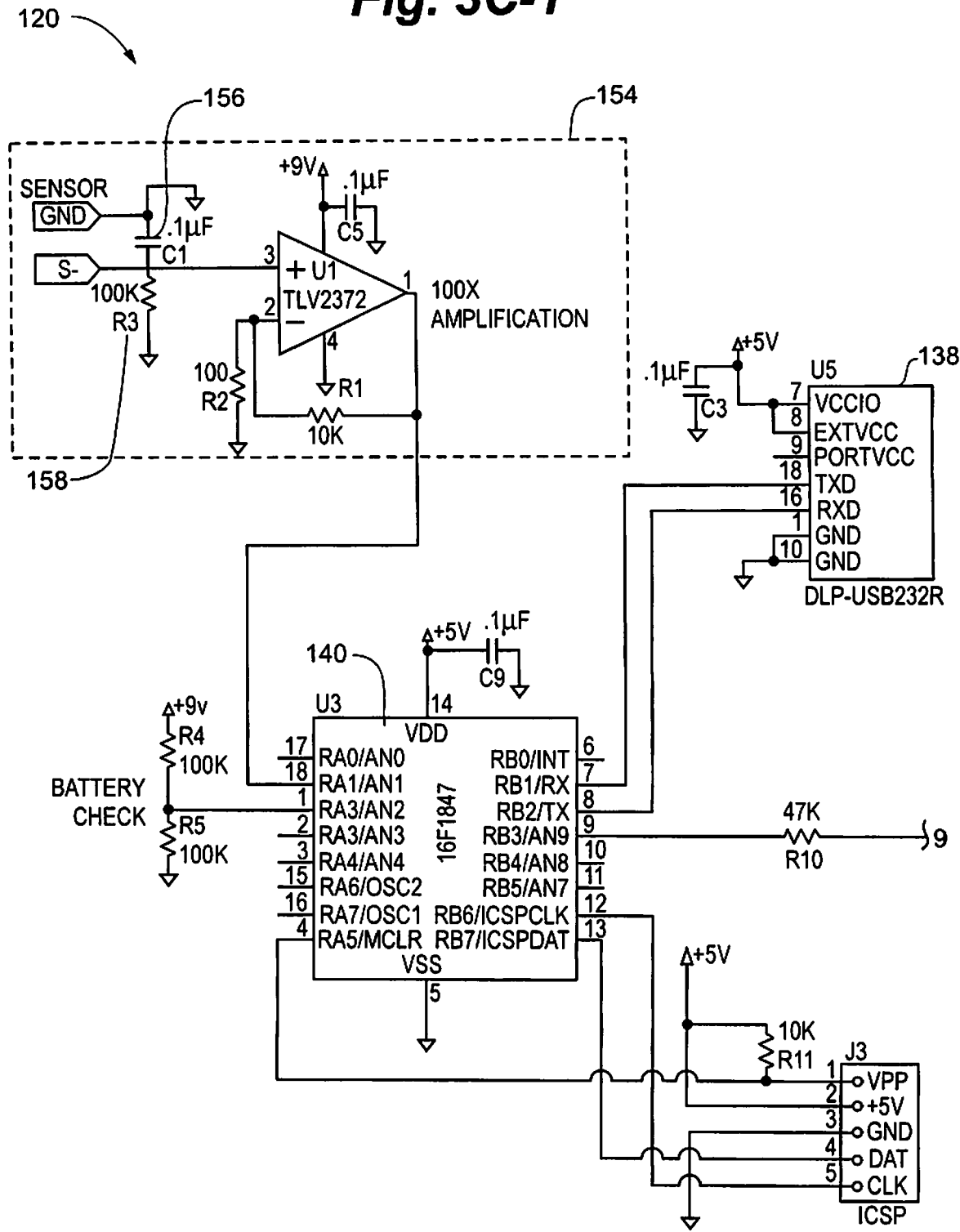
FIG. 3C is a circuit schematic diagram of the stimulator device of FIGS. 3A and 3B.
Figures 2, 3C:
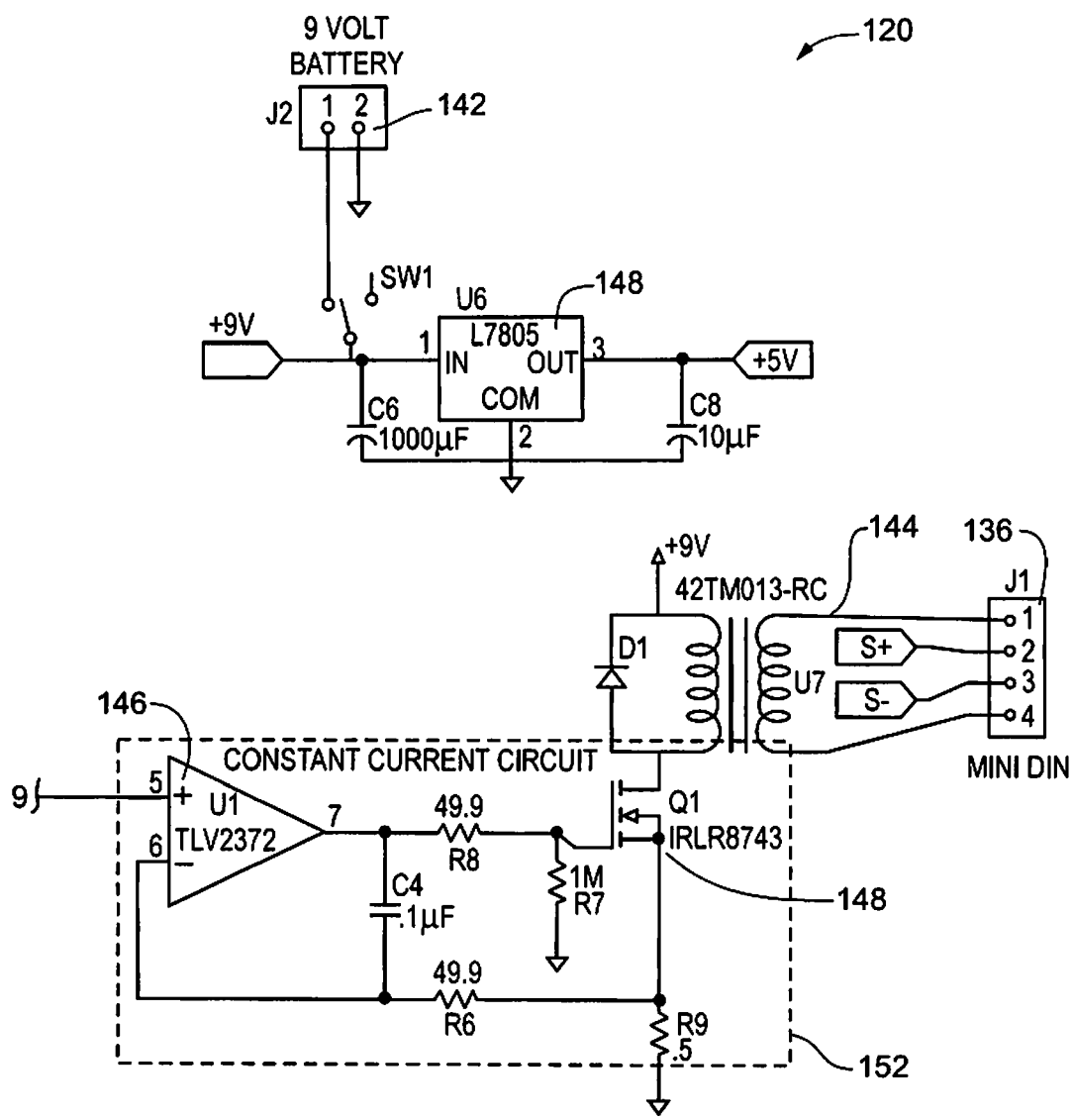

Referring also to FIG. 3C, op amp 146, MOSFET 148 and other circuitry can form a constant current circuit 152, coupled between transformer 144 (which is in turn coupled with adapter 136) and microcontroller 140. Constant current circuit 152 and transformer 144 are utilized to send electrical pulses to the nerve(s) of the patient through electrodes 114 of patch device 110. Whenever a digital high signal is sent by microcontroller 140 to the input of constant current circuit 152, electrodes 114 will provide a surge of power that will activate the nearest nerves. Microcontroller 140, with computing device 130, controls the timing of the stimulation and the strength by using pulse width modulation (PWM) on the input to constant current circuit 146. Using constant current can be advantageous in embodiments because a nerve is activated depending on the amount of current it sees. Since the resistance of the electrode-skin interface can be variable from one person to the next, it can be important that the same amount of current is sent through electrodes 114 to cause the same amount of nerve activation in each patient, a muscle response to which can be sensed by sensor 116.

The resulting output sensed by sensor 116 can be amplified by a 100-times gain circuit 154. Microcontroller 140 can use a 10-bit ADC to measure the sensor, but only immediately after the stimulation of the muscle has occurred in one embodiment. Microcontroller 140 can find the maximum sensor readings of each electrical pulse. As previously mentioned, sensor 116 can be piezoelectric, a passive sensor comprising two different materials that create a voltage proportional to the amount of mechanical deflection sensed. To improve the sensor signal, a capacitor 156 can be used in between the input and output of sensor 116 to reduce the oscillating noise amplitude, and a pull down resistor 158 can be used to reduce or remove any direct current offset sensor 116 might experience.

Figures 1, 3E:
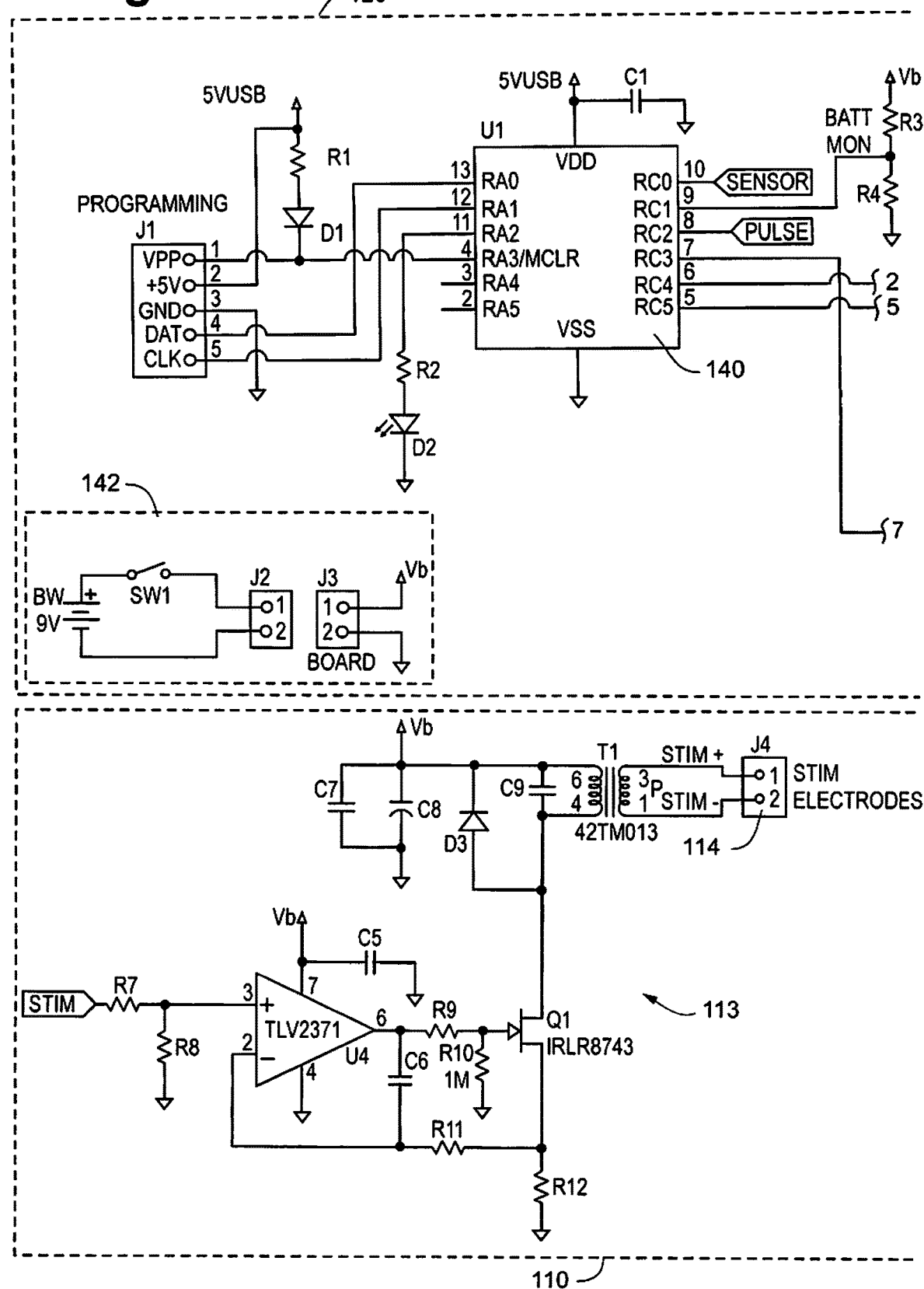
FIG. 3E is a schematic depiction of the diagram of FIG. 3D.
Figures 2, 3E:
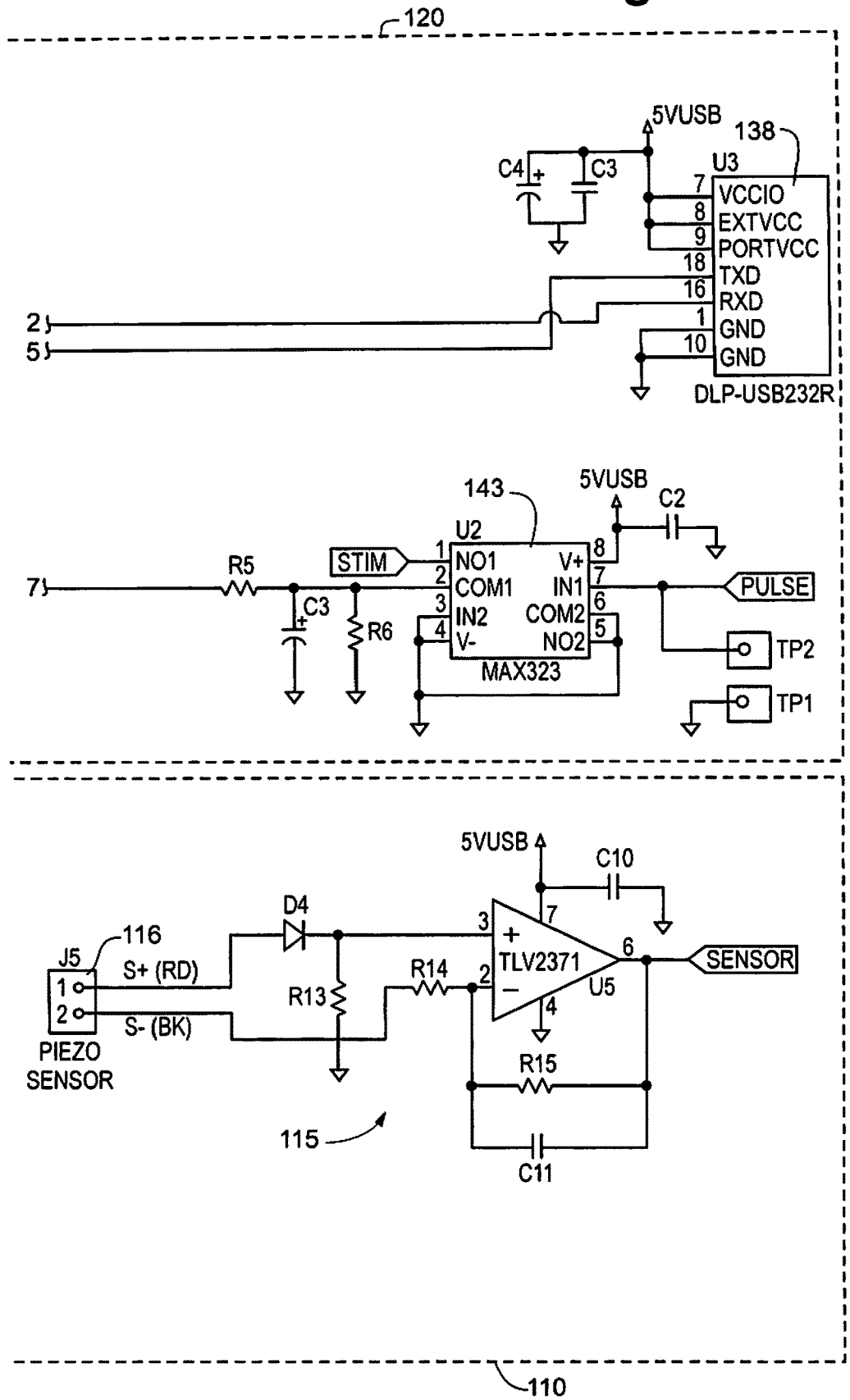

FIGS. 3D and 3E are additional depictions of an embodiment of patch device 110 and stimulator device 120. Couplings and connections shown in FIG. 3D can be actual physical connections, functional connections or both, such as those depicted in FIG. 3E. For example, while four connections are shown between stimulator device 120 and patch device 110 in FIG. 3D, only two wires may physically couple stimulator device 120 and patch device 110 to accomplish the four connections depicted. In that way, the connections can comprise functions or abilities to communicate between different devices and components, and those functions or communications can take place via shared or the same physical couplings, such as via wires or wirelessly. Additionally, what is depicted in FIGS. 3D and 3E is but one example embodiment, and the components, couplings and/or connections can vary in other embodiments.

In an embodiment, stimulator device 120 comprises microcontroller 140, such as a PIC16F1825 14-pin microchip available from MICROCHIP TECHNOLOGY or another comparable or suitable microcontroller device. Microcontroller 140 comprises inputs for programming, such as via computing device 130 or some other device or methodology.

Stimulator device 120 also comprises power source 142, such as a battery (e.g., 9 V), external power connection (e.g., to 120 V or 220 V) or some other power source. Power source 142 is coupled with patch device 142 in embodiments to provide power for stimulation via electrodes 114 and, optionally, sensing via sensor 116. In other embodiments, sensor 116 and circuitry 115 can be powered via a USB connection or other source. If power source 142 comprises a battery, microcontroller 140 can be coupled to the battery to monitor the status of the battery and provide an output related thereto (e.g., an LED that indicates that suitable power is available or that lights when power is below some threshold programmed into microcontroller 140). In embodiments, microcontroller 140 can be powered via the battery, or via a USB, AC or other connected power source, rather than power source 142 when power source 142 comprises a battery, to reserve battery power for stimulation.

In embodiments, stimulator device 120 comprises USB adapter 138, such as a DLP-USB232R mini USB-UART adapter available from DLP DESIGN or another comparable or suitable USB adapter or adapter for another communication technology. USB adapter 138 can couple stimulator device 120 with patch device 110 (and sensor circuitry 115 in particular) and/or computing device 130 to provide, receive and/or exchange stimulation, sensing and other operational data before, during or after operation, as well as power (e.g., 5 V) for stimulator device 120 itself in embodiments.

Stimulator device 120 can comprise a switch 143 in embodiments. In one embodiment, switch 143 can comprise a MAX323 single-supply, SPST analog switch available from MAXIM or another comparable or suitable switch or switching device. In embodiments, switch 143 is coupled between microcontroller 140 and the stimulation circuitry 113 and electrodes 114 of patch device 110. In this way, in operation, when microcontroller sends a "PULSE" signal to switch 143, switch 143 in turn provides a "STIM" signal to stimulation circuitry 113 of patch device 110. Circuitry 113 can comprise amplifiers, a transformer, capacitors, resistors, transistors, diodes and other circuitry arranged to transform the "STIM" signal from switch 143 to stimulation pulse(s) via electrodes 114. In one embodiment, the transformer can comprise a 42TM013 transformer available from XICON or another comparable or suitable transformer or circuitry. The transformer can provide positive and negative stimulation pulses to electrodes 114 (e.g., a positive stimulation pulse to a first one of electrodes 114 and a negative stimulation pulse to the other of electrodes 114, in an embodiment).

In embodiments, microcontroller 140 can be coupled with sensing circuitry 115 of patch device 110 to send signals to and/or receive signals and data from sensor 116. In embodiments, this can be a direct coupling (e.g., via a wire 117a or 117b), coupling via USB adapter 138 (which also can be via wire 117a and/or 117b in some embodiments, or some other way in other embodiments), both a direct coupling and a coupling via USB adapter 138, or some other arrangement or configuration.

Figure 4:
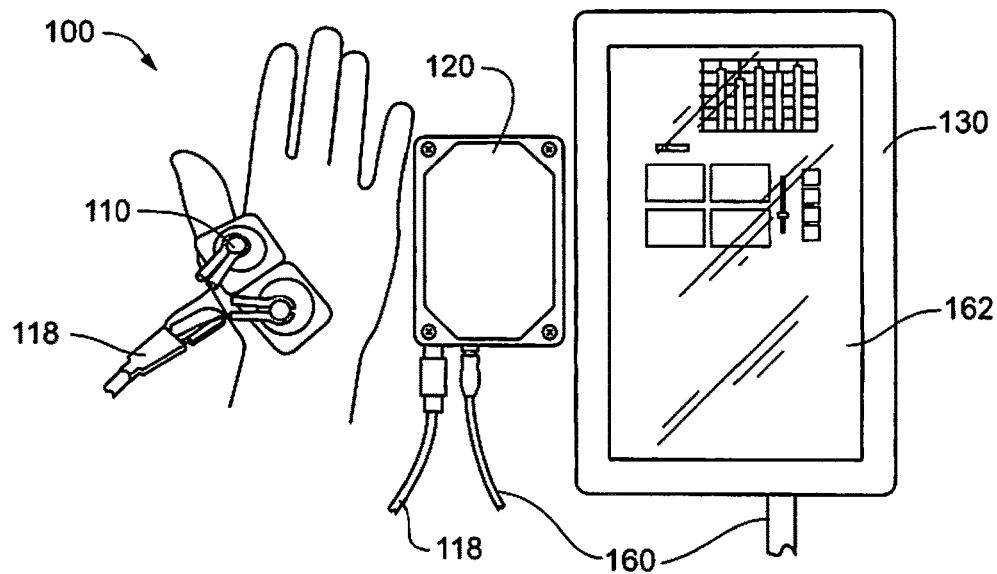
FIG. 4 is a depiction of a working prototype of a neuromuscular blockage monitoring system according to an embodiment.
Figure 5:
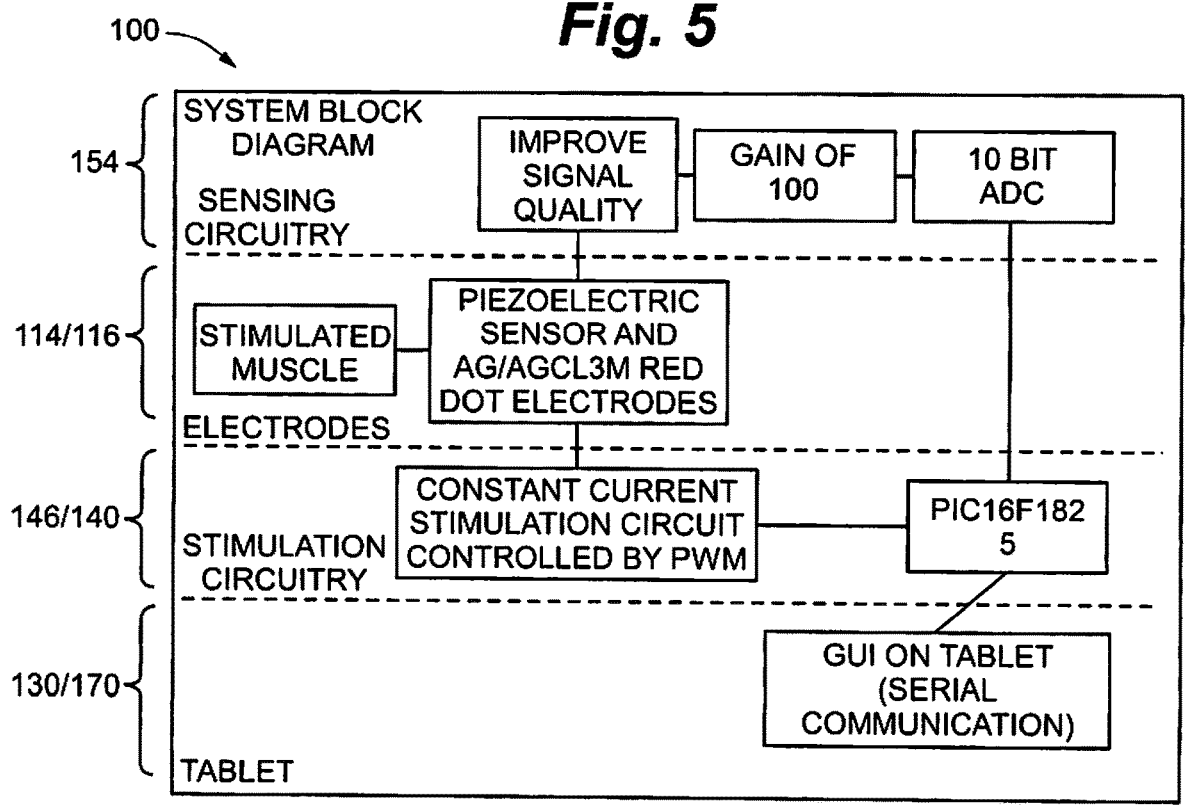
FIG. 5 is a system block diagram of a neuromuscular blockage monitoring system according to an embodiment.

Referring to FIGS. 4 and 5, stimulator device 120 can communicate with computing device 130 via a cable 160, which in one embodiment comprises a USB cable with suitable connectors for interfacing with each stimulator device 120 (e.g., a mini B male connector for interfacing with port 128) and computing device 130 (e.g., a male USB connector). Stimulator device 120 can communicate with computing device 130 over asynchronous serial communication. Data can be sent two bytes at a time, with one sending 8-bit data and another sending an 8-bit command, in one embodiment. Data can be placed in a buffer that can be checked continuously, and if data exists on the buffer it can be read and cleared. In embodiments, cable 160 also can provide power to stimulator device 120, such as 5V via USB.

Figure 6:
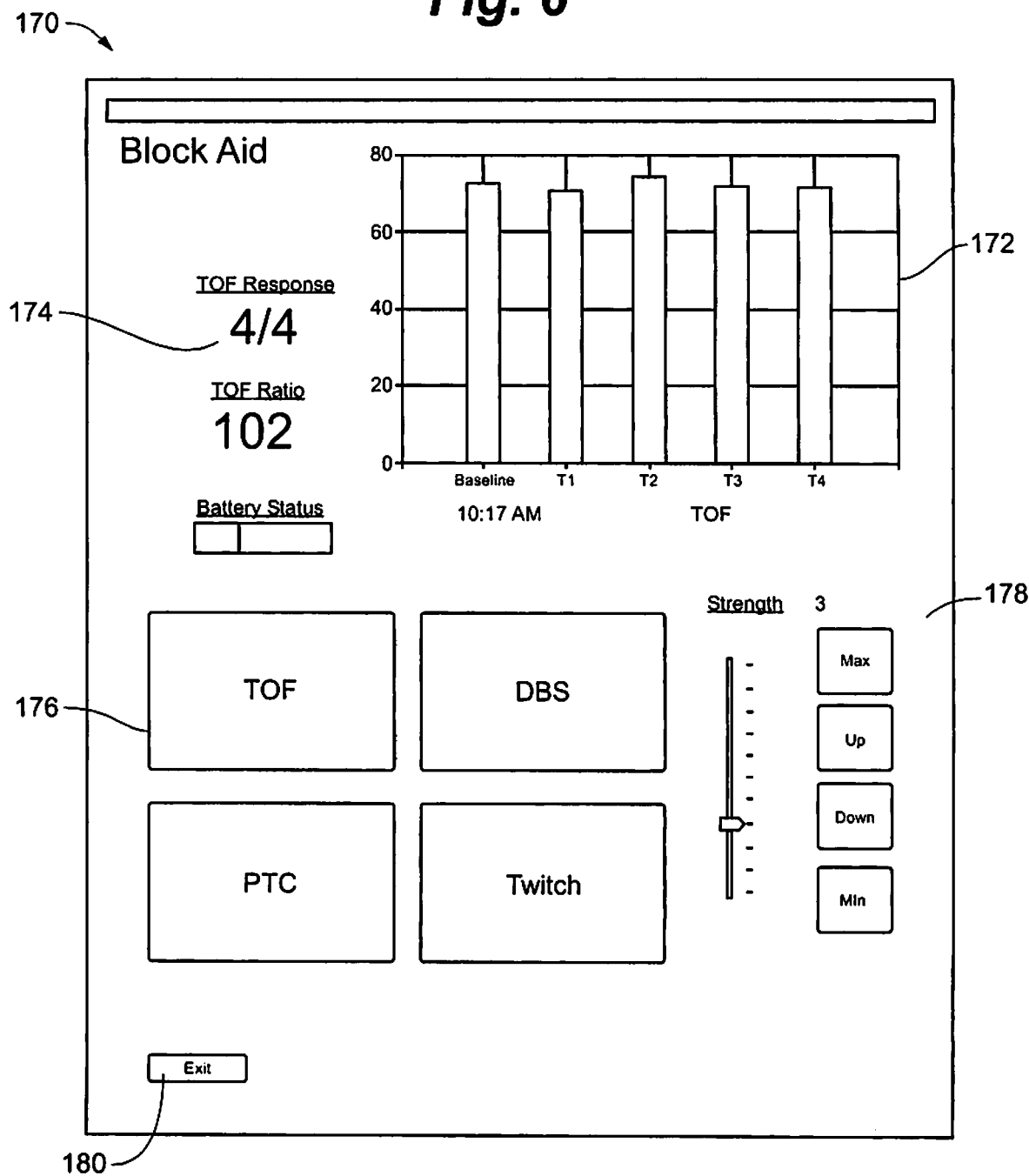
FIG. 6 is a screenshot of a graphical user interface (GUI) of a neuromuscular blockage monitoring system according to an embodiment.
Figure 7:
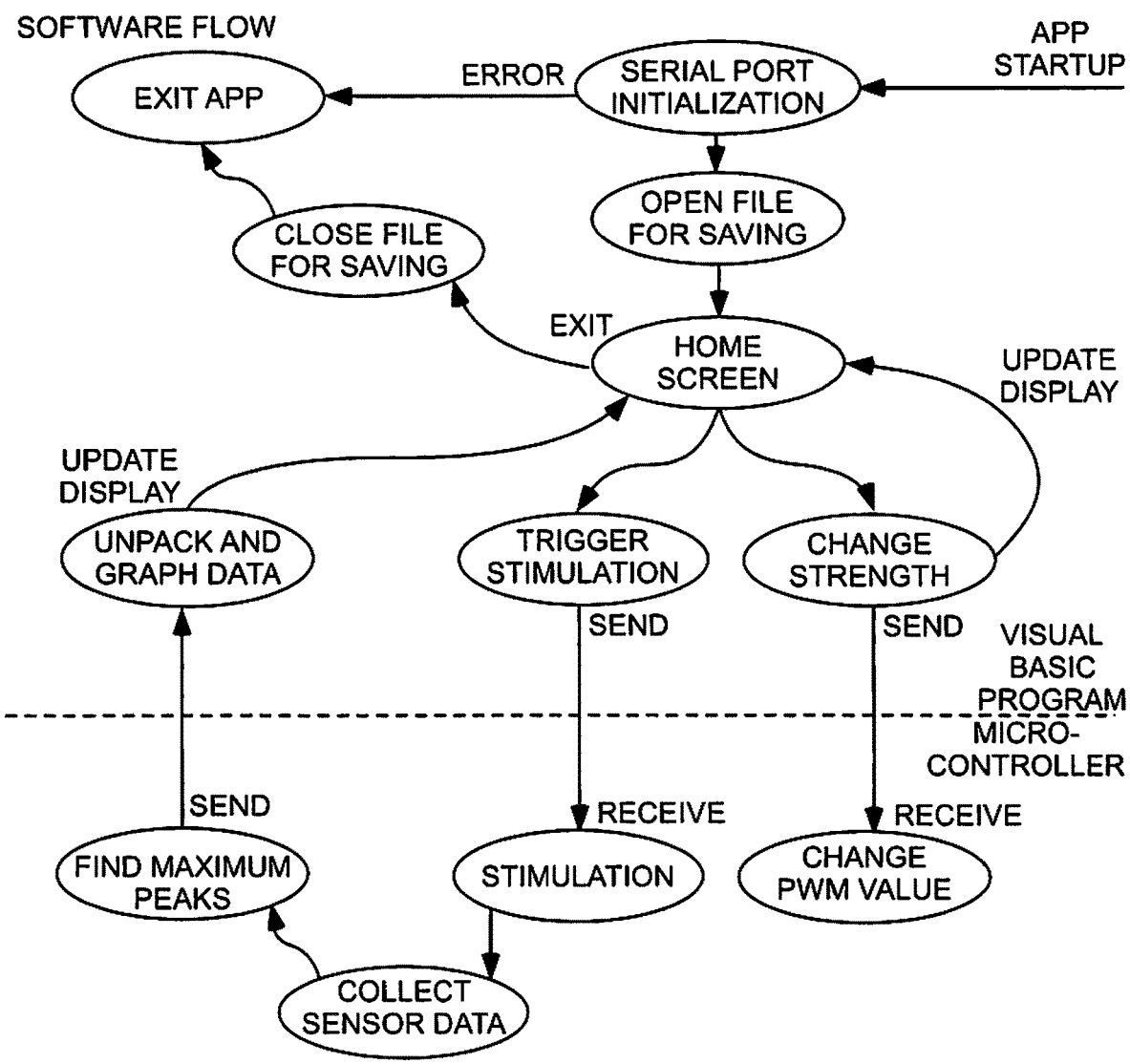
FIG. 7 is a software flow diagram of a neuromuscular blockage monitoring system according to an embodiment.

Referring also to FIGS. 6 and 7, computing device 130 can comprise a suitable program, such as an application (or "app") using visual basic or other software or programming, providing a graphical user interface (GUI) 170 on a display 162 to enable a user to operate and interact with system 100 via computing device 130. One example GUI 170 is depicted in FIG. 6. GUI 170 can be designed to mimic the button layout of a traditional PNS that a user may be accustomed to, while at the same time providing additional intuitive displays and features to provide information previously obtained only manually. For example, GUI 170 includes a TOF and baseline data display 172 of the muscle twitch readings for the current TOF measurement as well as the average strength of the initial TOF measurement or baseline. A metrics display 174 can include a response indicator of how many of the four stimulations of the TOF test resulted in a sensed muscular response as well as a result of a calculation of the TOF ratio. Stimulation buttons 176 can be provided to select and initiate one or more different stimulation routines. As depicted in FIG. 6, a TOF test has been selected, but GUI 170 can enable a user to select other test methodologies, such as double burst stimulation (DBS), post tetanic count (PTC), single twitch, and others. A strength control and display portion 178 can enable a user to adjust stimulation strength, while also displaying the currently selected strength. An exit button 180 also can be provided to close the app and/or save data, such as to a .csv or other file. In still other embodiments, button 180 or another feature can cause the program or app to automatically save and/or send data to an EMR, medical server or network, or other device, in conjunction with exiting GUI 170 or separately, such as midway through a procedure, in which case GUI can further comprise a "save" button in addition to exit button 180. In still other embodiments, GUI 170 can be configured to automatically save and/or transfer data after each test, periodically or according to some other timing.

In yet another embodiment, GUI 170, the underlying app or software, or some other feature of computing device 130 and/or system 100 can further comprise at least one input device, such as a physical keyboard or a graphical keyboard operable via a touchscreen feature of computer device 130, a mouse, a touchscreen feature, a barcode or QR code reader, a scanner, an audio or video feature like a camera, or some other input device. Such an input device can enable a user to enter relevant patient or procedural data or otherwise interact with system 100 to match data obtained by system 100 with an EMR or other document or system.

Figure 8:
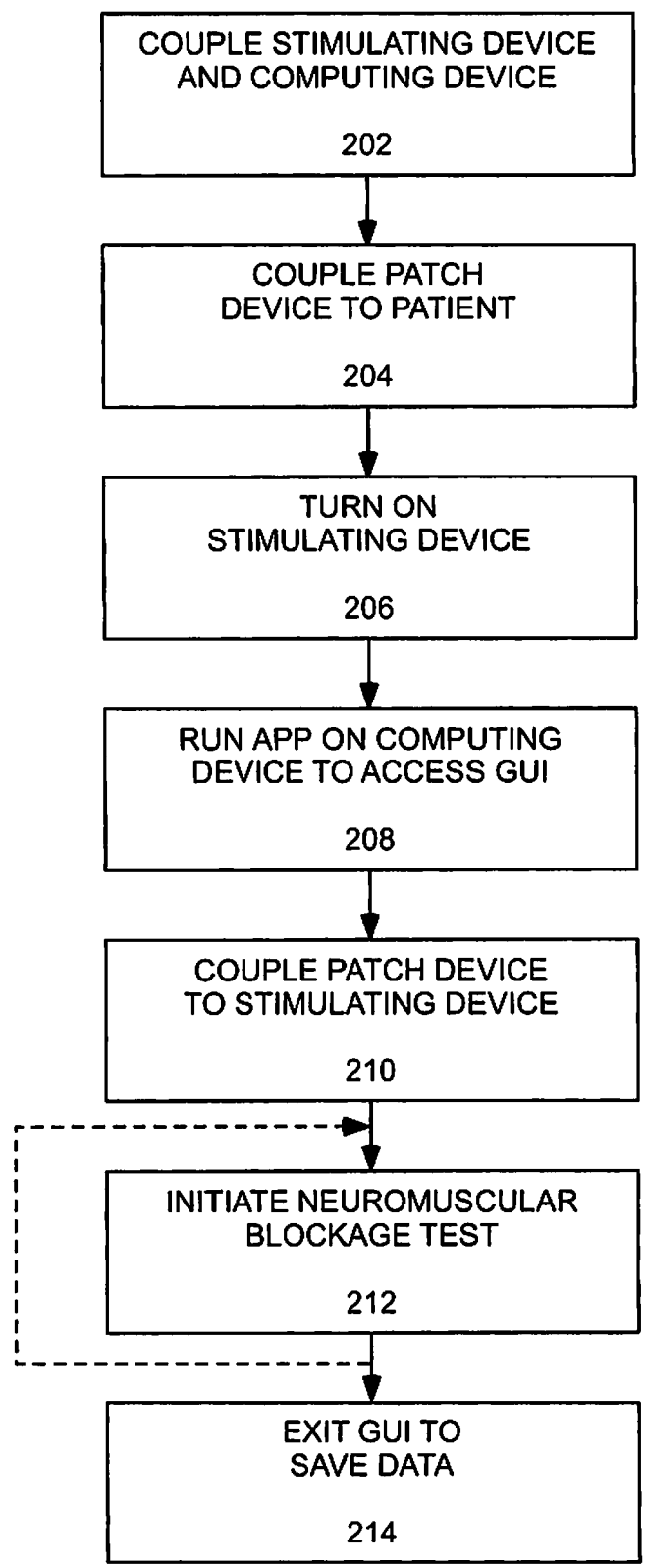
FIG. 8 is a flow diagram of a method related to a neuromuscular blockage monitoring system according to an embodiment.

Referring also to FIG. 8, in use stimulator device 120 and computer device 130 are communicatively coupled with one another, such as via cable 160 or wirelessly, at 202. At 204, patch device 110 is coupled to a patient, such as by removing a backing layer of patch device 110 to expose an adhesive layer, and affixing the adhesive layer to a patient's skin proximate any convenient motor point. At 206, stimulator device 120 is turned on, such as via switch 124, and at 208 the app and GUI 170 are run on computing device 130. At 210, patch device 110 and stimulator device 120 are operatively coupled with one another, such as via cable 118. At 212, at least one neuromuscular blockage test, such as a TOF test, is initiated via GUI 170, and this may be repeated one or more times throughout a surgical or other procedure. Once complete, data can be saved and GUI 170 exited at 214, at which point patch device 110 can be removed from the patient and disposed of, while stimulator device 120 and computing device 130 can be powered off.

The order of the tasks or events in FIG. 8 can be changed in other embodiments, and other tasks and events can be added before, within or after those shown in FIG. 8. For example, the order of 202 and 204 can be reversed, or data can be saved as part of or after 212 but before 214. After 214, a report or other documentation can be run and/or a summary screen presented via GUI 170 to summarized some of all of the stimulation or sensor events that occurred during a particular time or procedure.

In embodiments, GUI 170 can also provide access to diagnostic or troubleshooting information, such as to calibrate sensor 116, stimulator device 120 or some other component of system 100. GUI 170 can also provide a user guide, instructions, help screens, diagnostics, self-test and contact information and functionality that can be useful to a user before, during or after a procedure. In still other embodiments, GUI 170 can be programmed to remind a user using an audio and/or visual cue to initiate a neuromuscular blockage test periodically, such as every fifteen minutes or according to a frequency associated with a surgical procedure, patient characteristic, a facility or other best practice, or some other characteristic.

In embodiments, the app, software or program underlying GUI 170 can be obtained via the internet, such as via an app store or a website. In one embodiment, a kit comprising at least one patch device and the stimulator device further comprises instructions or an access code for obtaining the app, software or program. For example, the kit can comprise a code that a user can enter in an app store or on a website to initiate a free download of the app, software or program. In still other embodiments, the app, software or program can be provided via a computer-readable medium, such as a CD, disk, USB drive or other fixed tangible media.

While embodiments discussed herein relate to patient neuromuscular blockage monitoring, such as during surgical procedures, other embodiments can be used beyond such monitoring and/or outside of surgical settings and procedures, such as for relative assessment of various muscle forces in an ICU patient, among others. This could provide insights into drug levels, loss of contractions due to edema or other causes, etc., by performing motor point stimulation of various muscle groups. Various other uses and applications are also possible, in these and other embodiments. Other uses contemplated include veterinary uses.

In embodiments, computing device 130, microprocessors and other computer or computing devices discussed herein can be any programmable device that accepts digital data as input, is configured to process the input according to instructions or algorithms, and provides results as outputs. In an embodiment, computing device 130 and other such devices discussed herein can be, comprise, contain or be coupled to a central processing unit (CPU) configured to carry out the instructions of a computer program. Computing device 130 and other such devices discussed herein are therefore configured to perform basic arithmetical, logical, and input/output operations.

Computing device 130 and other devices discussed herein can include memory. Memory can comprise volatile or non-volatile memory as required by the coupled computing device 130 or processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the invention.

In embodiments, the system or components thereof (e.g., computing device 130, stimulation device 120 or other devices or components) can comprise or include various engines, each of which is constructed, programmed, configured, or otherwise adapted, to autonomously carry out a function or set of functions. The term "engine" as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A neuromuscular blockage monitoring system comprising:
    a patch device comprising a unitary patch body, at least two electrodes and at least one sensor, the at least one sensor arranged between the at least two electrodes on the unitary patch body; and
    a stimulator device operatively coupled to the patch device and configured to provide at least one electrical signal to the at least two electrodes to stimulate a muscle motor point proximate the patch device such that a result detectable by the at least one sensor is produced, and the stimulator device is further configured to receive a signal from the at least one sensor related to the result produced by the at least two electrodes stimulating the muscle motor point, such that the patch device both stimulates the muscle motor point and detects the result of the stimulation of the muscle motor point;
    the at least one sensor including a piezoelectric sensing element configured to detect the result; and
    a computing device communicatively coupled to the stimulator device and configured to determine a level of neuromuscular blockage from the signal from the at least one sensor.

2. The system of claim 1, wherein the computing device comprises a display to present a graphical user interface (GUI).

3. The system of claim 2, wherein the GUI is used to initiate provision of the at least one electrical signal to the at least two electrodes by the stimulator device.

4. The system of claim 3, wherein the GUI is configured to present a graphical representation of the signal from the at least one sensor related to a result of the stimulation of the muscle motor point.

5. The system of claim 4, wherein the stimulator device is configured to provide a series of four electrical signals comprising a Train of Four (TOF) test, and the GUI is configured to display a graphical representation of the series of four electrical signals.

6. The system of claim 5, wherein the GUI is configured to display at least one metric related to the TOF test.

7. The system of claim 6, wherein the at least one metric comprises at least one of a baseline pulse strength, a number of responses detected by the at least one sensor, or a TOF ratio.

8. The system of claim 1, wherein the computing device is configured to generate a data file related to the result of the stimulation of the muscle motor point.

9. The system of claim 8, wherein the computing device is configured to communicate the data file or information from the data file to an electronic medical record (EMR).

10. The system of claim 1, wherein at least two of the patch device, the stimulator device and the computing device communicate with each other wirelessly.

11. The system of claim 1, wherein the patch device is configured to be removably coupled to a patient's skin proximate a muscle motor point.

12. The system of claim 11, wherein the unitary patch body further comprises an adhesive layer to removably couple the patch device to a patient's skin.

13. The system of claim 1, wherein the stimulator device is operatively coupled to the patch device by two wires.

14. The system of claim 1, wherein the stimulator device further comprises a battery power source.

15. The neuromuscular blockage monitoring system of claim 1, wherein the at least one sensor is selected from the group consisting of a vibration sensor and a stretch sensor.

16. A kit comprising:
    at least one patch device comprising a unitary patch body, at least two electrodes and at least one sensor, the at least one sensor arranged between the at least two electrodes on the unitary patch body, the at least one sensor having a piezoelectric sensing element;
    a stimulator device operatively coupled to the at least one patch device and configured to provide at least one electrical signal to the at least two electrodes to stimulate a muscle motor point proximate the at least one patch device such that a result detectable by the at least one sensor is produced, and the stimulator device is further configured to receive a signal from the at least one sensor related to the result produced by the at least two electrodes stimulating the muscle motor point, such that the at least one patch device both stimulates the muscle motor point and detects, via the at least one sensor having the piezoelectric sensing element, the result of the stimulation of the muscle motor point;
    a computing device communicatively coupled to the stimulator device and configured to determine a level of neuromuscular blockage from the signal from the at least one sensor; and
    user instructions related to the at least one patch device, the stimulator device, and the computing device.

17. The kit of claim 16, further comprising at least one cable configured to couple with the stimulator device.

18. The kit of claim 16, wherein the user instructions comprise a hardcopy manual.

19. The kit of claim 16, wherein the user instructions comprise information to access a digital user instruction file.

20. The kit of claim 16, further comprising at least one of instructions or an access code for obtaining software to interface with the stimulator device.

* * * * *